United States Patent [19]

Degenhardt

[11] Patent Number: 4,939,284

[45] Date of Patent: Jul. 3, 1990

[54] PROCESS FOR THE MANUFACTURE OF TETRAALKYL ETHENYLIDENEBISPHOSPHONATE ESTERS

[75] Inventor: Charles R. Degenhardt, Cincinnati, Ohio

[73] Assignee: The Procter & Gamble Company, Cincinnati, Ohio

[21] Appl. No.: 300,990

[22] Filed: Jan. 24, 1989

Related U.S. Application Data

[60] Division of Ser. No. 855,877, Apr. 23, 1986, Pat. No. 4,820,698, which is a continuation-in-part of Ser. No. 795,306, Nov. 4, 1985, abandoned.

[51] Int. Cl.$^5$ ............................................. C07F 9/32
[52] U.S. Cl. ................................. 558/142; 558/161
[58] Field of Search ........................................ 558/142

[56] References Cited

U.S. PATENT DOCUMENTS

| | | | |
|---|---|---|---|
| 3,062,792 | 11/1962 | McConnell et al. | 558/161 |
| 3,544,509 | 12/1970 | Carroll et al. | 562/21 |
| 3,576,793 | 4/1971 | Carroll et al. | 562/21 |
| 3,671,644 | 6/1972 | Irani et al. | 424/346 |

FOREIGN PATENT DOCUMENTS 1204967 12/1970 United Kingdom .

OTHER PUBLICATIONS

McIntosh et al., Can. J. Chem., vol. 56 (1978), pp. 226–231.
Patai et al., J. Org. Chem., vol. 25 (1960, pp. 1232–1234).
Semmalhack et al., J. Org. Chem., 43(6), pp. 1259–1262 (Mar. 1978).
Degenhardt et al., J. Org. Chem., 51(18), pp. 3488–3490 (Sep. 1986).

*Primary Examiner*—Anton H. Sutto
*Attorney, Agent, or Firm*—Leonard W. Lewis; David K. Dabbiere; Steven J. Goldstein

[57] ABSTRACT

Disclosed are tetraalkyl enthenylidenebisphosphonates and a method for their manufacture. These compounds are suitable for use as antimicrobial agents in combating a number of pathogenic microorganisms, such as bacteria, yeasts, viruses, fungi and protozoa, when used together with a pharmaceutically-acceptable carrier. Also disclosed is a method for treating infectious diseases by administering a safe and effective amount of these tetraalkyl ethenylidenebisphosphonates.

9 Claims, No Drawings

PROCESS FOR THE MANUFACTURE OF TETRAALKYL ETHENYLIDENEBISPHONATE ESTERS

CROSS-REFERENCE TO RELATED APPLICATIONS

This is a division of application Ser. No. 855,877, filed on Apr. 23, 1986, now application Ser. No. 4,820,698 which is a continuation-in-part of application Ser. No. 795,306, filed on Nov. 4, 1985, now abandoned.

TECHNICAL FIELD

This invention relates to certain novel antimicrobial agents useful in combating bacteria, yeasts, viruses, fungi and protozoa. More particularly, it relates to tetraalkyl ethenylidenebisphosphonates which have antimicrobial activity, to pharmaceutical compositions comprising those antimicrobial agents, to a method of using those agents therapeutically in humans and animals for the treatment of infectious diseases, and to a novel process for the manufacture of these tetraalkyl ethenylidenebisphosphonate antimicrobial agents.

BACKGROUND OF THE INVENTION

Numerous antimicrobial agents have been developed which are effective in treating a variety of pathogenic bacteria. Generally, the functional utility of these agents can be classified into three groups based on their general antimicrobial activity:

(1) drugs which are primarily effective against the gram-positive cocci and bacilli, which tend to have a relatively narrow spectrum of activity, including penicillin G, the semisynthetic penicillinase-resistant penicillins, the macrolides, the lincomycins, vancomycin, and bacitracin; (2) drugs which are primarily effective against the aerobic gram-negative bacilli, which include the aminoglycosides and polymyxins; and (3) relatively broad spectrum drugs which affect both the gram-positive and gram-negative bacilli, including the broad-spectrum penicillins (ampicillin and carbenicillin), the cephalosporins, the tetracyclines, chloro-amphenicol, trimethoprin and the sulfonamides.

When the antimicrobial activity of a compound is first tested, patterns of sensitivity and resistance are usually defined. However, the efficacy spectrum can subsequently vary markedly due to the fact that microorganisms can acquire resistance to antimicrobial agents, which allows them to survive in the presence of these antibiotics. In order to overcome this problem, strong impetus exists for the development of new antimicrobial agents.

It has been found that certain novel tetraalkyl ethenylidenebisphosphonates are effective against a broad spectrum of gram-positive and gram-negative microorganisms, such as bacteria, yeasts, viruses, fungi and protozoa, many of which are resistant to the widely used antimicrobials, such as penicillin. These tetraalkyl ethenylidenebisphosphonates can be used to control and eliminate the infectious agents responsible for diseases such as gas gangrene, dental caries, urinary tract infections, gastrointestinal infections, vaginal infections and skin infections. Additionally, the efficacy of these compounds is not significantly affected by the presence of human serum.

Accordingly, it is an object of the present invention to provide certain novel tetraalkyl ethenylidenebisphosphonates which are highly active against a number of pathogenic microorganisms.

A further object of the present invention is to provide pharmaceutical compositions comprising these tetraalkyl ethenylidenebisphosphonates along with a pharmaceutically-acceptable carrier. Still a further object of the present invention is to provide a method of using these tetraalkyl ethenylidenebisphosphonates in the treatment in humans or animals of infectious diseases caused by pathogenic microorganisms. Still a further object of the present invention is to provide a novel one-pot process for the preparation of these tetraalkyl ethenylidenebisphosphonates.

BACKGROUND ART

McIntosh et al., *Canadian Journal of Chemistry*, Vol 56 (1981) pp. 226–31, discloses the preparation of vinyl phosphates from diethyl carbomethoxy methyl phosphonate, paraformaldehyde, methanol, piperdine and toluenesulfonic acid.

A two-step process for the manufacture of ethylene-1,1-diphosphonic acid is disclosed in Great Britain Patent No. 1,204,967, published Sept. 9, 1970. In Step 1, 1-hydroxyethane-1,1-diphosphonic acid is converted to its sodium salt. In Step 2, ethylene -1,1-diphosphonic acid is prepared from the corresponding salt at temperatures of from 200° C. to 500° C. These compounds are disclosed as being useful as sequestering agents, chelating agents, water-treating agents, stabilizers for peroxy compounds, additives in liquid soaps, detergents and shampoo, agents for use in scouring cloth, metal, rubber and plastic compositions, dairy cleaning compositions, agents for use in pulp and paper processing, corrosion inhibitors, feed and vegetation supplements, herbicides, insecticides, metal treating compositions, electroplating, detergent builders for anionic, nonionic, and/or amphoteric synthetic detergents, lime soap dispersants, surfactants, dispersants for clays, drilling muds, paper pulps, inorganic and organic pigments, and cement slurries, bactericide potentiators, hair modifiers in shampoos, fertilizers, food and beverage acidulants, leavening agents, cheese emulsifiers, modifying agents in evaporated and condensed milk, flame retardants in paints, oil additives, gasoline additives and dentrifice compositions. It is taught that this acid can be reacted with triethyl orthoformate to produce tetraethyl ethene -1,1-disphosphonate.

U.S. Pat. No. 3,062,792 to McConnell et al., issued Nov. 6, 1962, discloses the synthesis of certain flame retarding polymeric tetraalkyl vinylidenediphosphonates by the pyrolysis of tetraalkyl 1-acetoxy-ethene-1,1-diphosphonates at temperatures ranging from 450° C. to 500° C.

SUMMARY OF THE INVENTION

This invention comprises tetraalkyl ethenylidenebisphosphonate esters of the formula:

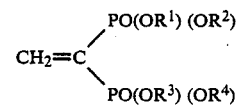

wherein $R^1$, $R^2$, $R^3$ and $R^4$ are individually selected from the group consisting of $C_1$ to $C_7$ straight or branched alkyl. Also covered are pharmaceutical compositions comprising a safe and effective amount of these tetraalkyl ethenylidenebisphosphonates together with a pharmaceutically-acceptable carrier.

This invention also provides a method for treating infectious diseases in humans and animals by administering a safe and effective amount of these tetraalkyl ethenylidenebisphosphonates.

This invention further provides a method for manufacturing these same tetraalkyl ethenylidenebisphosphonates by:

(a) combining from about 20 to about 96 mole percent of a formaldehyde or formaldehyde precursor selected from the group consisting of formaldehyde, paraformaldehyde or trioxane; from about 2 to about 40 mole percent of a secondary amine; and from 2 to about 40 mole percent of a tetraalkyl methylenebisphosphonate of the formula:

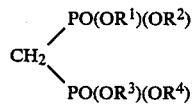

wherein $R^1$, $R^2$, $R^3$ and $R^4$ are independently chosen from the group consisting of $C_1$ to $C_7$ straight or branched alkyl; in an alcohol solvent selected from the group consisting of methanol and ethanol;

(b) heating said mixture to a temperature of from about 40° C. to about 80° C., for a period of from about 0.5 hours to about 200 hours;

(c) replacing said alcohol solvent with an equivalent amount of a solvent selected from the group consisting of toluene, benzene and xylene; and (d) adding a catalytic amount of an acid selected from the group consisting of paratoluenesulfonic acid and phosphoric acid, and allowing said mixture to react for a period of from about 2 hours to about 48 hours.

DETAILED DESCRIPTION OF THE INVENTION

The compositions and methods of this invention incorporate certain tetraalkyl ethenylidenebisphosphonates having the formula:

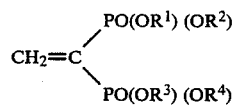

wherein $R^1$, $R^2$, $R^3$ and $R^4$ are independently chosen from the group consisting of $C_1$ to $C_7$ straight or branched chain alkyl, preferably, wherein when $R^1$, $R^2$, $R^3$ and $R^4$ are $C_1$ to $C_4$ straight or branched chain alkyl they are not all the same alkyl. That is, in one preferred embodiment $R^1$, $R^2$, $R^3$ and $R^4$ are not all $CH_3$ or $C_2H_5$ or $C_3H_7$ or $C_4H_9$ (although compounds where $R^1$, $R^2$, $R^3$, and $R^4$ are the same $C_1$–$C_4$ alkyl are also useful herein). Most preferred R groups are $C_1$ and $C_7$ straight chain alkyl.

Examples of tetraalkyl ethenylidenebisphosphonates useful in the present invention include
tetraisopropyl ethenylidenebisphosphonate,
tetra-n-pentyl ethenylidenebisphosphonate,
tetra-n-hexyl ethenylidenebisphosphonate,
tetraheptyl ethenylidenebisphosphonate,
diethyl dibutyl ethenylidenebisphosphonate,
dimethyl di-n-propyl ethenylidenebisphosphonate,
dimethyl diisopropyl ethenylidenebisphosphonate,
dimethyl di-n-butyl ethenylidenebisphosphonate,
diethyl di-n-propyl ethenylidenebisphosphonate,
diethyl diisopropyl ethenylidenebisphosphonate,
diethyl dimethyl ethenylidenebisphosphonate,
diethyl dibutyl ethenylidenebisphosphonate,
diethyl diisobutyl ethenylidenebisphosphonate,
dimethyl di-n-pentyl ethenylidenebisphosphonate,
diethyl di-n-pentyl ethenylidenebisphosphonate,
dimethyl di-n-hexyl ethenylidenebisphosphonate,
dimethyl di-n-heptyl ethenylidenebisphosphonate,
diethyl di-n-hexyl ethenylidenebisphosphonate,
diethyl di-n-heptyl ethenylidenebisphosphonate,
di-n-propyl di-n-butyl ethenylidenebisphosphonate,
di-n-propyl di-n-pentyl ethenylidenebisphosphonate,
methyl triethyl ethenylidenebisphosphonate,
methyl tri-n-propyl ethenylidenebisphosphonate,
methyl triisopropyl ethenylidenebisphosphonate,
methyl tri-n-butyl ethenylidenebisphosphonate,
ethyl tri-methyl ethenylidenebisphosphonate,
ethyl tri-n-propyl ethenylidenebisphosphonate,
ethyl tri-n-butyl ethenylidenebisphosphonate,
methyl tri-n-hexyl ethenylidenebisphosphonate,
methyl tri-n-pentyl ethenylidenebisphosphonate,
methyl tri-n-heptyl ethenylidenebisphosphonate,
ethyl tri-n-pentyl ethenylidenebisphosphonate,
ethyl tri-n-hexyl ethenylidenebisphosphonate and
ethyl tri-n-heptyl ethenylidenebisphosphonate.

The process of the present invention provides surprisingly higher yields and faster rates of reaction in the synthesis of tetraalkyl ethenylidenebisphosphonates than methods previously known in the art. In fact, the process of the present invention provides up to a 30% to 40% higher yield than the prior art processes. Typically, the process of the present invention provides a 70% to 80% yield of the final tetraalkyl ethenylidenebisphosphonate.

The tetraalkyl ethenylidenebisphosphonates described herein can be readily prepared using the following general synthetic scheme:

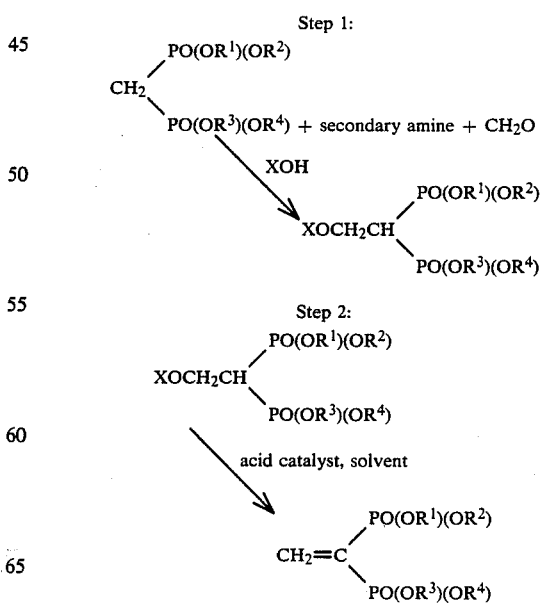

wherein $X = CH_3$ or $C_2H_5$.

Step 1

The compounds suitable for conversion to tetraalkyl ethenylidenebisphosphonates include tetraalkyl methylene-bisphosphonates (mixtures of these compounds may be used). As used herein, the term tetraalkyl methylenebisphosphonate refers to compounds having the formula:

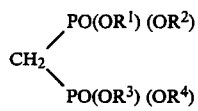

wherein $R^1$, $R^2$, $R^3$ and $R^4$ are individually selected from the group consisting of $C_1$ to $C_7$ straight or branched alkyl. A particularly preferred tetraalkyl methylenebisphosphonate for use in this process is tetraethyl methylenebisphosphonate. Other preferred methylenebisphosphonates suitable for use in the method of the present invention include tetramethyl methylenebisphosphonate, tetraisopropyl methylenebisphosphonate, tetra-n-propyl methylenebisphosphonate, tetra-n-butyl methylenebisphosphonate, tetra-n-pentyl methylenebisphosphonate and tetra-n-hexyl methylenebisphosphonate. All of these tetraalkyl methylenebisphosphonates are commercially available compounds.

It is to be understood that $R^1$, $R^2$, $R^3$ and $R^4$ may be the same or different alkyl groups. For example, $R^1$ and $R^2$ may be $CH_3$ and $R^3$ and $R^4$ may be $C_2H_5$ in which case the suitable starting ester would be diethyl dimethyl methylenebisphosphonate,

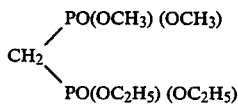

Other examples of such tetraalkyl methylenebisphosphonates are diethyl dibutyl methylenebisphosphonate, dimethyl di-n-propyl methylenebisphosphonate, dimethyl diisopropyl methylenebisphosphonate, dimethyl di-n-butyl methylenebisphosphonate, diethyl di-n-propyl methylenebisphosphonate, diethyl diisopropyl methylenebisphosphonate, diethyl dimethyl methylenebisphosphonate, diethyl diisobutyl methylenebisphosphonate, dimethyl di-n-pentyl methylenebisphosphonate, diethyl di-n-pentyl methylenebisphosphonate, dimethyl di-n-hexyl methylenebisphosphonate, dimethyl di-n-heptyl methylenebisphosphonate, diethyl di-n-hexyl methylenebisphosphonate, diethyl di-n-heptyl methylenebisphosphonate, di-n-propyl di-n-butyl methylenebisphosphonate, di-n-propyl di-n-pentyl methylenebisphosphonate, methyl triethyl methylenebisphosphonate, methyl tri-n-propyl methylenebisphosphonate, methyl triisopropyl methylenebisphosphonate, methyl tri-n-butyl methylenebisphosphonate, methyl tri-n-pentyl methylenebisphosphonate, methyl tri-n-hexyl methylenebisphosphonate, methyl tri-n-heptyl methylenebisphosphonate, ethyl tri-methyl methylenebisphosphonate, ethyl tri-n-propyl methylenebisphosphonate, ethyl tri-n-butyl methylenebisphosphonate, ethyl tri-n-pentyl methylenebisphosphonate, ethyl tri-n-hexyl methylenebisphosphonate and ethyl tri-n-heptyl methylenebisphosphonate.

Such tetraalkyl methylenebisphosphonate starting materials can be readily synthesized by the procedure set forth in Bartlett et al., *J. Org. Chem.* Vol. 47, 1284–1291 (1982), and also by the procedure set forth in Worms et al., "Organic Phosphorus Compounds", Vol. 7, p. 22–36 (1976), both of which are incorporated by reference herein.

In the method of the present invention, the above-described tetraalkyl methylenbisphosphonate is added to formaldehyde, in the form of formaldehyde (neat or in solution), paraformaldehyde $(CH_2O)_n$, or trioxane,

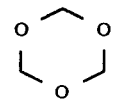

(preferably paraformaldehyde), and a secondary amine, such as pyrrolidine, piperidine, diethylamine, dimethylamine, benzylmethylamine, dibenzylamine, di-n-butylamine, dicyclohexylamine, di-n-hexylamine, diisobutylamine, diisopropylamine, di-n-octylamine or piperazine. Preferably the amine is diethylamine, piperidine or pyrrolidine, which have been shown to react most favorably with a variety of the tetraalkyl methylenebisphosphonates. The most preferred amine is diethylamine.

Typically, this mixture comprises from about 2 to about 40 mole percent of the tetraalkyl methylenebisphosphonate combined with from about 2 to about 40 mole percent of the amine and from about 20 to about 96 mole percent of formaldehyde. Preferably, from about 10 to about 20 mole percent of tetraalkyl methylene bisphosphonate is combined with from about 10 to about 20 mole percent of the amine and from about 50 to about 80 mole percent of formaldehyde. Most preferably, from about 10 to about 15 mole percent of the tetraalkyl methylenebisphosphonate is combined with from about 10 to about 15 mole percent of the amine and from about 50 to about 75 mole percent of the formaldehyde.

An intermediate compound,

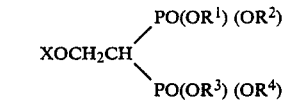

is formed by refluxing the above reactants in an alcohol solvent, such as ethanol or methanol, preferably methanol, typically at a temperature of from about 40° C. to about 80° C. Temperatures much below 40° C. do not provide effective conversion as the rate of reaction would be too slow. Temperatures of from about 55° C. to about 75° C. typically provide optimum conversion.

This reaction is carried out for a period of time sufficient to provide the desired degree of conversion. The reaction time generally depends upon the tetraalkyl methylenebisphosphonate being used, the particular amine and alcohol solvent selected, as well as the ratio of the starting materials selected. It has been found that reactions utilizing tetraethyl and tetramethyl methylenebisphosphonate as the starting material generally form the intermediate within from about 0.5 hours to about 48 hours, whereas larger esters and branched alkyl esters, such as tetraisopropyl methylenebisphosphonate can take from about 50 hours to about 200 hours to form the intermediate.

This intermediate can be characterized by NMR and mass spectroscopy. For example, when the starting material is tetraethyl methylenebisphosphonate, and the alcohol solvent is methanol, the intermediate has the following spectroscopic characteristics: $^1$H NMR (CDCl$_3$) 4.02 (m, 8H, —OCH$_2$CH$_3$, J=7.3), 3.63 (dd, 2H, CH$_3$OCH$_2$—, J=5.4 and 15.6, 3.20 (s, 3H, CH$_3$O—), 2.52 (tt, 1H, PCHP, J=6.0 and 24.0), 1.18 (t, 12H, —CH$_2$CH$_3$, J=7.1); $^{13}$C NMR (CDCl$_3$) 67.8 (t, CH$_3$OCH$_2$-, J=4.4), 62.2 (d, —OCH$_2$CH$_3$, J=4.4), 58.3 (s, CH$_3$O—), 38.5 (t, PCP, J=132.4), 16.0 (d, —OCH$_2$CH$_3$, J=7.4); $^{31}$P NMR (CDCl$_3$) +21.0; ammonia Cl mass spectrum m/e 350 (M+NH$_4$)+.

After reflux, the reaction mixture (the intermediate) is then diluted with an alcohol, preferably methanol or ethanol, to lower the concentration of the amine before it is removed. It has been found that if the amine is not first diluted, it produces impurities in the final tetraalkyl ethylidenebisphosphonate product. It is preferable to dilute the reaction mixture such that it has an amine concentration of about 0.1 to about 0.5 molar. The alcohol and the amine are then removed by, for example, distillation under vacuum or by other methods commonly known in the art.

Step 2

The intermediate is dissolved in a hydrocarbon solvent, such as toluene, benzene or xylene. Preferred is toluene. The hydrocarbon solvent is added to the intermediate in a concentration of from about 0.5 to about 5 molar, preferably about 0.5 to about 2 molar.

A catalytic amount of an acid catalyst selected from the group consisting of paratoluenesulfonic acid and phosphoric acid, or mixtures thereof, is then added to catalyze the elimination of alcohol from the intermediate as depicted below:

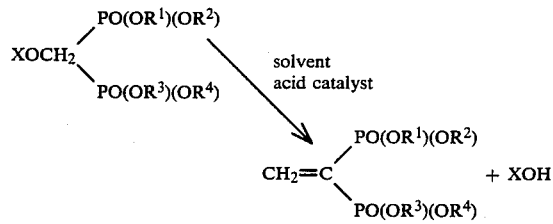

What is "a catalytic amount" can vary depending upon the acid catalyst being used, the tetraalkyl methylenebisphosphonate being converted, the particular solvent, the reaction conditions during the elimination (e.g., temperature), and like factors. It has been found that an amount from about 0.1 to about 1.0 mole percent of the acid catalyst based on the amount of the intermediate typically provides optimum elimination of the alcohol from the intermediate.

Typically, this reaction is carried out at reflux temperature for from about 2 to about 72 hours. For example, when toluene is the solvent, reflux temperature is from about 100° C. to about 120° C. and the reaction takes from about 2 to 48 hours.

Finally, the desired end product is separated from the reaction mixture and, when appropriated, purified. The eliminated alcohol may be removed by distillation or by molecular sieve, both of which are common methods known in the art for removing alcohols.

The resulting solution can be concentrated by a variety of conventional methods, such as a rotary evaporator. If desired, purification of the tetraalky ethenylidenebisphosphonate can be accomplished by diluting the resulting concentrate with an organic solvent, such as chloroform, methylene chloride or diethyl ether, and then extracted with water.

The organic solvent can then be removed by, for example, distillation under vacuum. The resulting tetraalkyl ethenylidenebisphosphonate is further purified by any of a variety of methods known in the art. Examples of such purification methods include distillation and chromatography.

COMPOSITIONS

The compositions of the present invention comprise:
(a) a safe and effective amount of a tetraalkyl ethenylidenebisphosphonate ester of the present invention, or mixtures of such esters; and
(b) a pharmaceutically-acceptable carrier.

A safe and effective amount of the tetraalkyl ethenylidenebisphosphonate is that amount which eliminates the infecting organism thereby alleviating the infectious disease at a reasonable benefit/risk ratio, as is attendant with any medical treatment. Obviously, the amount of the tetraalkyl ethylidenebisphosphonate or mixture which is administered will vary with such factors as the nature and severity of the particular disease being treated, the duration of the treatment, the route of administration, the physical condition of the patient, the nature of concurrent therapy (if any), the specific formulation and carrier employed, and the solubility and concentration of tetraalkyl ethylidenebisphosphonate used, as well as the pharmacokinetics of that compound.

As used herein the term "pharmaceutically-acceptable carrier" denotes a solid or liquid filler, diluent, or encapsulating substance. Examples of substances which can serve as pharmaceutical carriers for tetraalkyl ethenylidenebisphonates include: sugars, such as lactose, glucose and sucrose; starches, such as corn starch and potato starch; cellulose and its derivatives, such as sodium carboxymethylcellulose, ethyl cellulose, cellulose acetate, powdered tragacanth; malt; gelatin; talc; stearic acid; magnesium stearate; calcium sulfate; vegetable oils, such as peanut oil, cottonseed oil, sesame oil, olive oil, corn oil and oil of theobroma; polyols, such as propylene glycol, glycerin, sorbitol, mannitol, and polyethylene glycol; sugar; alginic acid; pyrogen-free water; isotonic saline; phosphate buffer solutions; cocoa butter (suppository base); emulsifiers, such as polysorbate 80, as well as other non-toxic compatible substances typically used in pharmaceutical formulations.

The pharmaceutical carrier employed in conjunction with the tetraalkyl ethenylidenebisphosphonate is used at a concentration sufficient to provide a practical size to dosage relationship. Preferably, the pharmaceutical carrier comprises about 0.01% to about 95% by weight of the total composition.

Various oral dosage forms can be used, including such solid forms as tablets, capsules, granules, bulk powders and microcapsules of the drug. These oral forms comprise a safe and effective amount, from about 0.01% to about 95%, and preferably from about 0.1% to about 50%, of the tetraalkyl ethylidenebisphosphonate. Tablets can be compressed, enteric-coated, sugar-coated or film-coated, and contain suitable binders, lubricants, surfactants, diluents, disintegrating agents, coloring agents, flavoring agents, preservatives, flow-inducing agents, and melting agents, as appropriate. Liquid oral dosage forms include aqueous and nonaqueous solutions, emulsions, suspensions, solutions and/or suspensions reconstituted from non-effervescent granules, containing suitable solvents, preservatives, emulsifying agents, suspending agents, diluents, sweeteners, melting agents, coloring agents, and flavoring agents. Preferred carriers for oral administration include gelatin, propylene glycol, ethyl oleate, cottonseed oil, sesame oil and polysorbate 80. Specific examples of pharmaceutically-acceptable carriers and excipients that may be used in formulating oral dosage forms of the present invention are described in U.S. Pat. No. 3,903,297, Robert, issued Sept. 2, 1975, incorporated by reference herein. Techniques and compositions for making solid oral dosage forms are described in Marshall, "Solid Oral Dosage Forms", *Modern Pharmaceutics* (Banker and Rhodes, editors) Vol. 7, 359–427 (1979), incorporated herein by reference. Techniques and compositions for making tablets (compressed, formulas and molded), capsules (hard and soft gelatin) and pills are described in *Remington's Pharmaceutical Sciences* (Arthur Osol, editor), 1553–1593 (1980), incorporated herein by reference.

The compositions of the present invention can also be administered topically, i.e., by the direct laying on or spreading of the composition on epidermal or epithelial tissue. Such compositions may be formulated as lotions, creams, ointments, solutions, gels or solids. A highly preferred composition contains the tetraalkyl ethenylidenebisphosphonate in a soap matrix. These topical compositions comprise a safe and effective amount, usually from about 0.1% to about 20%, and preferably from about 1% to about 10%, of the tetraalkyl ethylidenebisphosphonate. Suitable carriers for topical administration preferably remain in place on the skin as a continuous film and resist being washed off easily by perspiration or by immersion in water. Generally, the carrier is either organic in nature or an aqueous emulsion and is capable of having the tetraalkyl ethylidenebisphosphonate dispersed, dissolved or suspended therein. The tetraalkyl ethenylidenebisphosphonates of the present invention can also be used in combination with other compatible pharmaceuticals. The carrier may include pharmaceutically-acceptable emollients, skin penetration enhancers, coloring agents, fragrances, emulsifiers, thickening agents, and solvents. A more detailed description of such forms follows:

1. Lotions

The lotions can comprise a safe and amount of the tetraalkyl ethenylidenebisphosphonate; from about 0.1% to 25%, preferably from about 3% to about 15%, of an emollient; the balance being water, a $C_2$ or $C_3$ alcohol, or a mixture of water and the alcohol. Examples of suitable emollients are as follows:

1. Hydrocarbon oils and waxes. Examples are mineral oil, petrolatum, paraffin, ceresin, ozokerite, microcrystalline wax, polyethylene, and perhydrosqualene.

2. Silicone oils, such as polydimethylsiloxanes, methylphenylpolysiloxanes, water-soluble and alcohol-soluble silicone-glycol copolymers.

3. Triglyceride fats and oils, such as those derived from vegetable, animal and marine sources. Examples include castor oil, safflower oil, cotton seed oil, corn oil, olive oil, cod liver oil, almond oil, avocado oil, palm oil, sesame oil, and soybean oil.

4. Acetoglyceride esters, such as acetylated monoglycerides.

5. Ethoxylated glycerides, such as ethoxylated glyceryl monostearate.

6. Alkyl esters of fatty acids having 10 to 20 carbon atoms. Methyl, isopropyl and butyl esters of fatty acids are especially useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

7. Alkenyl esters of fatty acids having 10 to 20 carbon atoms. Examples thereof include oleyl myristate, oleyl stearate, and oleyl oleate.

8. Fatty acids having 9 to 22 carbon atoms. Suitable examples include pelargonic, lauric, myristic, palmitic, stearic, isostearic, hydroxystearic, oleic, linoleic, ricinoleic, arachidonic, behenic, and erucic acids.

9. Fatty alcohols having 10 to 22 carbon atoms. Lauryl, myristyl, cetyl, hexadecyl, stearyl, isostearyl, hydroxystearyl, oleyl, ricinoleyl, behenyl, erucyl, and 2-octyl dodecyl alcohols are examples of suitable fatty alcohols.

10. Fatty alcohol ethers. Ethoxylated fatty alcohols of 10 to 20 carbon atoms include the lauryl, cetyl, stearyl, isostearyl, oleyl, and cholesterol alcohols having attached thereto from 1 to 50 ethylene oxide groups or 1 to 50 propylene oxide groups, or a mixture thereof.

11. Ether-esters such as fatty acid esters of ethoxylated fatty alcohols.

12. Lanolin and its derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.

13. Polyhydric alcohols and polyether derivatives. Propylene glycol, dipropylene glycol, polypropylene glycol (M.W. 2000–4000), polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol (M.W. 200–6000), methoxy polyethylene glycols, poly[ethylene oxide] homopolymers (M.W. 100,000–5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), $C_{15}$–$C_{18}$ vicinal glycol, and polyoxypropylene derivates of trimethylolpropane are examples thereof.

14. Polyhydric alcohol esters. Ethylene glycol mono- and di-fatty acid esters, diethylene glycol mono- and di-fatty acid esters, polyethylene glycol (M.W. 200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

15. Wax esters, such as beeswax, spermaceti, myristyl myristate, stearyl stearate.

16. Beeswax derivatives, e.g., polyoxyethylene sorbitol beeswax. These are reaction products of beeswax with ethoxylated sorbitol of varying ethylene oxide content, forming a mixture of ether-esters.

17. Vegetable waxes including carnauba and candelilla waxes.

18. Phospholipids, such as lecithin and derivatives.

19. Sterols. Cholesterol, cholesterol fatty acid esters are examples thereof.

20. Amides, such as fatty acid amides, ethoxylated fatty acid amides, solid fatty acid alkanolamides.

The lotions further comprise from about 1% to 10%, preferably from about 2% to 5%, of an emulsifier. The emulsifiers can be nonionic, anionic or cationic. Examples of satisfactory non-ionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene oxide, mono- and di-fatty acid esters of ethylene glycol wherein the fatty acid moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan and hydrophilic wax esters. Suitable anionic emulsifiers include the fatty acid soaps, e.g. sodium, potassium and triethanolamine soaps, wherein the fatty acid moiety contains from 10 to 20 carbon atoms. Other suitable anionic emulsifiers include the alkali metal, ammonium or substituted ammonium alkyl sufates, alkyl arylsulfonates, an alkyl ethoxy ether sulfonates having 10 to 30 carbon atoms in the alkyl moiety. The alkyl ethoxy ether sulfonates contain from 1 to 50 ethylene oxide units. Satisfactory cationic emulsifiers are the quaternary ammonium, morpholinium and pyridinium compounds. Certain of the emollients described in preceding paragraphs also have emulsifying properties. When a lotion is formulated containing such an emollient, an additional emulsifier is not needed, though it can be included in the composition.

The balance of the lotion is water or a $C_2$ or $C_3$ alcohol, or a mixture of water and the alcohol. The lotions are formulated by simply admixing all of the components together. Preferably the tetraalkyl ethenylidenebisphosphonate is dissolved in the mixture. Conventional optional components can be included. One such additive is a thickening agent at a level from about 1% to 10% of the composition. Examples of suitable thickening agents include: cross-linked carboxypolymethylene polymers, ethyl cellulose, polyethylene glycols, gum tragacanth, gum kharaya, xanthan gums and bentonite.

2. Creams

Compositions of this invention also can be formulated in a cream form. The creams comprise safe and effective amount of the tetraalkyl ethenylidenebisphosphonate; from about 0.1% to 95%, preferably from about 10% to 25%, of an emollient; the balance being water. The emollients above described can also be used in the cream compositions. Optionally the cream form contains a suitable emulsifier, as previously described. When an emulsifier is included, it is in the composition at a level from about 3% to 50%, preferably from about 5% to 20%.

3. Solutions

The compositions of this invention can also be formulated as a solution. The solution form comprises a safe and effective amount of the tetraalkyl ethenylidenebisphosphonate, usually at least about 0.01% up to 95% and preferably about 0.1% to 10%; the balance being a suitable organic solvent. Suitable organic materials useful as the solvent or a part of a solvent system are as follows: propylene glycol, polyethylene glycol (M.W. 200–600), polypropylene glycol (M.W. 425–2025), glycerine, sorbitol esters, 1,2,6-hexanetriol, ethanol, isopropanol, diethyl tartrate, butanediol, and mixtures thereof. Such solvent systems can also contain water.

These solutions can be applied to the skin as is, or else can be formulated into, for example, an aerosol and sprayed onto the skin from an aerosol container, or a mouthwash composition and used as an oral rinse. The aerosol compositions further comprise from about 25% to 80%, preferably from about 30% to 50%, of a suitable propellant. Examples of such propellants are the chlorinated, fluorinated and chlorofluorinated lower molecular weight hydrocarbons. Nitrous oxide, carbon dioxide, butane, and propane may also be used as propellant gases. These propellants are used at a level sufficient to expel the contents of the container.

The carrier liquid in a mouthwash is generally a mixture of ethanol and water. The amount of ethanol is generally from about 5% to about 60%, preferably from about 5% to about 25% by weight of the carrier. Water then constitutes the remainder of the carrier liquid mixture. These mouthwash compositions can also contain other optional components such as emulsifying agents as previously described, flavoring agents, sweeteners and humectants. Other mouthwash formulations and methods for making mouthwashes useful in the present invention are disclosed in U.S. Pat. No. 4,323,551 to Parran, issued Apr. 6, 1982, which is incorporated by reference herein.

4. Gels

Compositions herein can be formulated into a gel form by simply admixing a suitable thickening agent to the previously described solution compositions. Examples of suitable thickening agents have been previously described with respect to the lotions.

The gelled compositions comprise a safe and effective amount of the tetraalkyl ethenylidenebisphosphonate, from about 0.01% to 95%, preferably from about 0.1% to 50%, of an organic solvent as previously described; from about 0.5% to 20%, preferably from about 1% to 10%, of the thickening agent; the balance being water.

5. Solids

The compositions of this invention can also be formulated in a solid form, e.g., a stick-type composition intended for application to the lips or other part of the body. Such compositions comprise a safe and effective amount of the tetraalkyl ethenylidenebisphosphonate and from about 0.01% to 98%, preferably from about 60% to 90%, of the previously described emollients. This composition can further comprise from about 1% to 20%, preferably from about 5% to 15%, of a suitable thickening agent, and optionally emulsifiers and water. Thickening agents previously described with respect to lotions are also suitable herein.

6. Soaps

The compositions of this invention can also be formulated into a soap matrix intended for washing infected wounds or burns or for sterilization of the skin for purposes such as surgical procedures. Such compositions comprise a safe and effective amount of the tetraalkyl ethenylidenebisphosphonate ranging from 0.1% to 20%; and from about 50% to 90% of an excipient such as those previously described. Optionally, the soap contains a suitable emulsifier as previously described. When an emulsifier is included, it is in the composition at a level from about 3% to about 50%, preferably from about 5% to about 20%.

7. Dentifrices

The compositions of this invention can also be formulated as dentifrices. Such dentifrices, especially toothpaste, comprise a safe and effective amount of the tetraalkyl ethenylidenebisphosphonate ranging from about 0.1% to about 20% by weight of the composition. Toothpaste compositions conventionally contain abrasive materials, sudsing agents, binders, humectants, flavoring and sweetening agents. Suitable dentifrice compositions and the methods of their manufacture useful in the present invention are fully set forth in U.S. Pat. No. 3,535,421 to Briner et al., issued Oct. 20, 1970, which is incorporated by reference herein.

8. Shampoos

Compositions of this invention also can be formulated in a shampoo form. The shampoos comprise a safe and effective amount of the tetraalkyl ethenylidenebisphosphonate ranging from about 0.1% to about 20%; from about 5% to about 60% of a synthetic surfactant; and the balance water. Suitable surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, lauryl sarcosine, cocoyl sarcosine, ammomium cocoyl sulfate, ammonium lauroyl sulfate, sodium cocoyl sulfate, sodium lauroyl sulfate, potassium cocoyl sulfate, potassium lauroyl sulfate, triethanolamine lauroyl sulfate, triethanolomine lauroyl sulfate, monoethanolamine cocoyl sulfate, monoethanolamine lauroyl sulfate, sodium tridecyl benzene sulfonate and sodium dodecyl benzene sulfonate.

These shampoos can contain a variety of nonessential optional components. Such conventional optional ingredients are well known to those skilled in the art, e.g., preservatives, such as benzyl alcohol, ethyl paraben, propyl paraben and imidazolidinyl urea; cationic surfactants, such as cetyl trimethyl ammonium chloride, lauryl trimethyl ammonium chloride, tricetyl methyl ammonium chloride, stearyldimethyl benzyl ammonium chloride, and di(partially hydrogentated tallow) dimethylammonium chloride; thickeners and viscosity modifiers such as a diethanolamide of a long-chain fatty acid (e.g. PEG 3 lauramide), block polymers of ethylene oxide and propylene oxide, sodium chloride, sodium sulfate, polyvinyl alcohol, and ethyl alcohol; pH adjusting agents, such as citric acid, succinic acid, phosphoric acid, sodium hydroxide, sodium carbonate; perfumes; dyes; and, sequestering agents, such as disodium ethylenediamine tetraacetate. Such agents generally are used individually at a level of from about 0.01% to about 10%, preferably from about 0.5% to about 5.0% by weight of the composition.

Additives commonly found in topical compositions, such as preservatives, e.g., methyl and ethyl-paraben, dyes and perfumes can be included in any of the previously described compositions.

The tetraalkyl ethenylidenebisphosphonates of the present invention are also useful when used systemically, for example by parenteral administration. These compounds are not significantly inactivated by human serum. The dosage of the tetraalkyl ethenylidenebisphosphonate which is both safe and effective to provide anti-infective activity will vary with the particular disease being treated, the severity of the disease, the duration of treatment, the specific tetraalkyl ethenylidenebisphosphonate employed and its usage concentration, and like factors within the specific knowledge and expertise of the attending physician and commensurate with a reasonable benefit/risk ratio associated with the use of any drug compound. Systemic compositions comprise a safe and effective amount, usually from about 0.01% to about 95% and preferably from 0.1% to 50% of the tetraalkyl ethenylidenebisphosphonate.

The tetraalkyl ethenylidenebisphosphonate can be administered parenterally in combination with a pharmaceutically acceptable carrier, such as corn oil, a camphor or sterile, pyrogen-free water, and optionally a water-miscible solvent (e.g., ethyl alcohol) at a practical amount of the tetraalkyl ethenylidenebisphosphonate per dose. Parenteral administration can be by subcutaneous, intradermal, intramuscular, intraarticular, or intravenous injection. The single dosage by these modes of administration is usually in the range of from about 0.1 mg to about 10 g per day. Obviously, multiple dosages will exceed this amount depending upon such factors as length of treatment and the severity of the condition being treated. Another factor to be considered is the serum half-life of the drug as it is being metabolized and excreted by the body, as measured by the attending physician. When the serum half-life is relatively short, such as less than 1 hour, then the drug dosage will be higher than if the half-life is longer, such as from 4 to about 12 hours.

METHOD OF TREATMENT

The present invention also encompasses methods of treating infectious diseases in humans or lower animals through administering, to the human or lower animal in need of such treatment, a safe and effective amount, usually from about 0.1 mg/kg to about 10,000 mg/kg per day, preferably from about 1 mg/kg to about 250 mg/kg per day, of a tetraalkyl ethenylidenebisphosphonate described herein. This amount can be given in a single dose or multiple doses repeatedly or sustained release dosages over the course of the treatment. While dosages higher than the foregoing are effective to treat infectious diseases, care must be taken, as with any drug, in some individuals to prevent adverse side effects. Generally, treatment with the tetraalkyl ethenylidenebisphosphonate will eliminate the infectious agent within seven to ten days.

The tetraalkyl ethenylidenebisphosphonate can be used to eliminate microorganisms which can cause a variety of infectious diseases in humans or animals, such as *Steptococcus mutans* which cause dental caries; *Clostridium perfingens* which cause gas gangrene; *Escherichia coli* or other enteric bacteria which cause urinary tract infections and gastrointestinal diseases; *Staphylococcus aureus*, which cause gastrointestinal disease and skin infections; *Staphylococcus aureus*, which cause vaginal infections; and *Escherichia coli Staphylococcus aureus* and *Proteus vulgaris*, which cause urinary tract infections.

The tetraalkyl ethenylidenebisphosphonate agents can be administered topically, orally, or systemically.

Topical administration can be used to treat infectious diseases through directly laying on or spreading a safe and effective amount of the tetraalkyl ethenylidenebisphosphonate, or composition containing a tetraalkyl ethenylidenebisphosphonate, on epidermal or epithelial tissue, including outer skin and oral, vaginal, gingival, nasal and inner-ear tissue. The amount of the agent to be topically administered may vary from about 0.01 mg/cm$^2$ to 5 mg/cm$^2$, and if a patch is worn over the affected area possibly lower concentrations, depending upon such factors as the sensitivity, type and location of tissue to be treated, the composition and carrier (if any) to be administered, and the particular tetraalkyl ethenylidenebisphosphonate to be administered as well as the particular disorder to be treated and the extent to which systemic (as distinguished from local) effects are desired. Generally, such patches are worn for not less than 1 hour. The extent of anti-infective efficacy also depends upon such factors as the amount of tetraalkyl ethenlidenebisphosphonate, the area of tissue to be covered, and the ability of the tetraalkyl ethenylidenebisphosphonate to penetrate the particular skin tissue.

Oral administration can be used to treat infectious diseases through oral dosing of a safe and effective amount of the tetraalkyl ethenylidenebisphosphonate of the present invention generally in a suitable oral pharmaceutical carrier. The tetraalkyl ethenylidenebisphosphonate is absorbed by the gastrointestinal tract. The compound may be formulated as a solid dosage form, such as tablets, hard gelatin capsules, soft gelatin capsules, bulk powders, sustained release formulations and microcapsules of the drug. Alternately, it may be formulated as a liquid dosage form, such as an aqueous or nonaqueous solution, emulsion or suspension.

The amount of the tetraalkyl ethenylidenebisphosphonate ingested depends upon the bioavailability of the compound from the oral pharmaceutical composition. Generally, the amount of the tetraalkyl ethenylidenebisphosphonate to be orally administered may vary from about 0.1 mg/kg/day to about 10,000 mg/kg/day and preferably from about 5 mg/kg/day to about 250 mg/kg/day. The amount of the pharmaceutical composition administered depends upon the percent of tetraalkyl ethenylidenebisphosphonate within its formula, which is a function of the amount of the tetraalkyl ethenylidenebisphosphonate required per dose, its stability, release characteristics and other pharmaceutical parameters.

Systemic administration can also be used to treat infectious diseases. Such administration may be intravenously, intramuscularly, intradermal, intraarterial, or subcutaneously. Generally, the amount of the tetraalkyl ethenylidenebisphosphonate to be systemically administered may vary from about 0.01 mg/kg/day to about 1000 mg/kg/day and preferably from about 0.1 mg/kg/day to about 250 mg/kg/day. The amount of pharmaceutical composition typically administered may vary from about 0.1 ml to about 5 ml of a solution or suspension of the tetraalkyl ethenylidenebisphosphonate in a pharmaceutically-acceptable carrier in a single dose. These compositions may also be administered systemically in multiple dosages, or by infusion.

The following non-limiting examples illustrate the synthesis procedure, compounds, compositions, and methods of treatment of the present invention.

EXAMPLE I

Tetraethyl ethenylidenebisphosphonate was made via the following synthetic procedure:

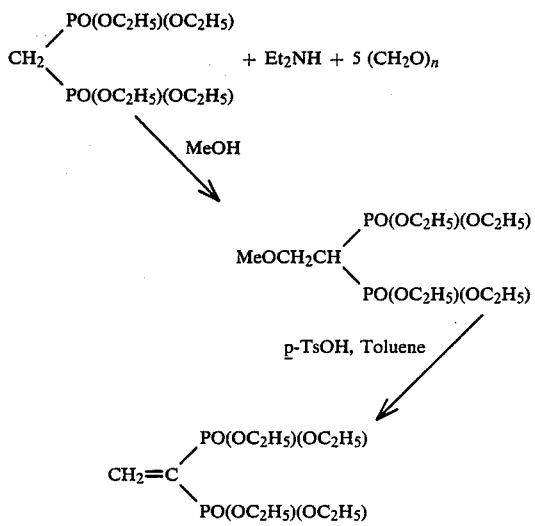

Specifically, 104.2 grams (3.47 mol) of paraformaldehyde and 50.8 (0.69 mol) of diethlamine were combined in 2 liters of methanol and the mixture warmed until clear. The heat was removed and 200.0 g (0.69 mol) of tetraethyl methylenebisphosphonate was added. The mixture was refluxed for 24 hours, then an additional 2 liters of methanol were added and the solution was concentrated under vacuum at 35° C. 1 liter of toluene was added and the solution again concentrated. This last step was repeated to ensure complete removal of methanol from the product which is obtained as a clear liquid. This intermediate was dissolved in 1 liter of dry toluene. p-toluenesulfonic acid monohydrate (0.50 g) was added to the mixture and this mixture was refluxed. Methanol was then removed from the reaction mixture by collection in a trap or by adsorption into 4A molecular sieves contained in a Soxhlet extractor. After 14 hours, the solution was concentrated. The crude product was diluted with 1 liter chloroform and washed with water (2×150 mL). The chloroform solution was dried over MgSO$_4$ and concentrated. After distillation 158.3 g of the tetraethyl ethenylidenebisphosphonate was produced as a clear liquid with the following spectral characteristics: $^1$H NMR (CDCl$_3$) 6.98 (distorted dd, 2H H$_2$C=, J=33.8 and 37.7), 4.32-4.00 (m, 8H, —OCH$_2$CH$_3$), 13.6 (t, 12H, —CH$_2$CH$_3$, J=7.1); $^{13}$C NMR (CDCl$_3$) 148.8 (s, H$_2$C=), 132.3 (t, PCP, J=166), 62.5 (d, —OH$_2$CH$_3$, J=2.9), 16.2 (d, OCH$_2$CH$_3$, J=2.9); $^{31}$P NMR (CDCl$_3$) +12.8.

EXAMPLE II

Tetramethyl ethenylidenebisphosphonate was synthesized via following general synthetic procedure.

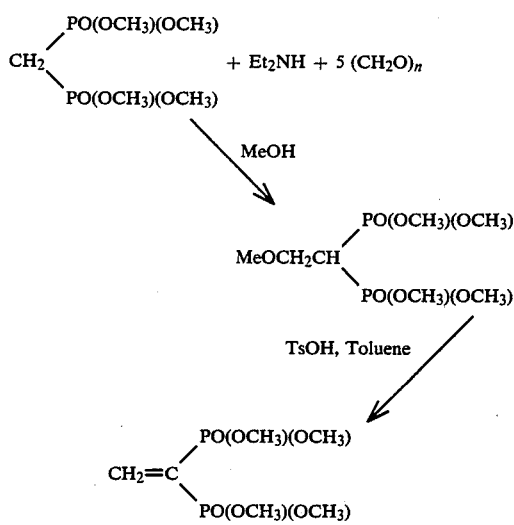

Specifically, 4.03 g (17.4 mmol) of tetramethyl methylenebisphosphonate, 2.60 g (86.7 mmol) of paraformaldehyde and 1.27 g (17.4 mmol) diethylamine were combined with the same reactants and at the same conditions as described above in Example I and refluxed for 2 hours. After the methanol was eliminated as described in Example I, 3.05 g of tetramethyl ethenylidenebisphosphonate was produced as a clear liquid with the following spectral characteristics: $^1$H NMR (CDCl$_3$) 6.99 (distorted dd, 2H H$_2$C=, J=33.9 and 37.7), (distorted dd, 12H, —OCH$_3$, J=5.1 and 6.1); $^{13}$C NMR (CDCl$_3$) 150.2 (s, H$_2$C=), 130.2 (t, PCP, J=168), 53.2 (s, —OCH$_3$); $^{31}$P NMR (CDCl$_3$) +15.5. Anal. Calcd for C$_5$H$_{14}$O$_6$P$_2$: C, 29.52; H, 5.78; P, 25.38. Found: C, 29.26; H, 6.01; P, 25.19.

EXAMPLE III

This example demonstrates the synthesis of tetraisopropyl ethenylidenebisphosphonate.

11.95 g (34.7 mmol) of tetraisopropyl methylenebisphosphonate, 5.2 g (173.5 mmol) of paraformaldehyde and 2.54 g (34.7 mmol) of diethylamine are combined with the same reactants and at the same conditions as described above in Example I. This mixture is then refluxed for 117 hours. After the methanol has been eliminated as described above in Example I, 3.0 g of tetraisopropyl ethenylidenebisphosphonate is produced as a clear liquid.

EXAMPLE IV

This example demonstrates the production of tetra-n-propyl ethenulidenebisphosphonate.

5.97 g (17.4 mmol) of tetra-n-propyl methylenebisphosphonate, 2.61 g (86.8 mmol) of paraformaldehyde and 1.27 g (17.4 mmol) of diethylamine are combined with the same reactants and the same conditions as described above in Example I. This mixture is then refluxed for 46 hours. After the methanol is eliminated as described above in Example I, 4.46 g of tetra-n-propyl ethenylidenebisphosphonate is produced as a clear oil.

EXAMPLE V

This example demonstrates the production of tetra-n-butyl ethenylidenebisphonate.

6.95 g (17.4 mmol) of tetra-n-butyl methylenebisphosphonate, 2.61 (86.8 mmol) of paraformaldehyde and 1.27 g (17.4 mmol) of diethylamine are combined with the same reactants and the same conditions as described above in Example I. This mixture is then refluxed for 46 hours. After the methanol is eliminated as described above in Example I, 4.72 g of tetra-n-butyl ethenylidenebisphosphonate is produced as a clear liquid.

EXAMPLE VI

This example demonstrates the production of tetra-n-pentyl ethenylidenebisphosphonate.

20.20 g (44.0 mmol) of tetra-n-pentyl methylenebisphosphonate, 6.61 g (220.0 mmol) of paraformaldehyde and 3.22 g (64.0 mmol) of diethylamine are combined with the same reactants and the same conditions as described above in Example I. This mixture is then refluxed for 48 hours. After the methanol is eliminated as described above in Example I. 14.08 g of tetra-n-pentyl ethenylidenebisphosphonate is produced as a clear liquid.

EXAMPLE VII

This example demonstrates the production of diethyl dimethyl ethenylidenebisphosphonate,

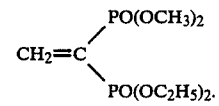

26.02 g (0.10 mmol) of diethyl dimethyl methylenebisphosphonate, 15.02 g (0.50 mmol) of paraformaldehyde and 7.31 g (0.10 mmol) of diethylamine are combined with the same reactants and the same conditions as described above in Example I. This mixture is then refluxed for 48 hours. After the methanol is eliminated as described above in Example I, about 20 g of diethyl dimethyl ethenylidenebisphosphonate is produced as a clear liquid.

EXAMPLE VIII

This example demonstrates the production of diethyl dimethyl ethenylidenebisphosphonate,

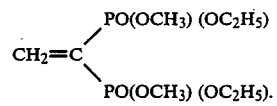

20.02 g (0.10 mmol) of diethyl dimethyl methylenebisphosphonate, 15.02 g (0.50 mmol) of paraformaldehyde and 7.31 g (0.10 mmol) of diethylamine are combined with the same reactants and the same conditions as described above in Example I. This mixture is then refluxed for 48 hours. After the methanol is eliminated as described above in Example I, about 20 g of diethyl dimethyl ethenylidenebisphosphonate is produced as a clear liquid.

EXAMPLE IX

Ths example demonstrates the production of dibutyl dimethyl ethenylidenebisphosphonate,

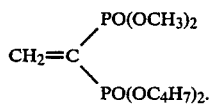

31.6 g (0.10 mmol) of dibutyl dimethyl methylenebisphosphonate, 15.02 g (0.50 mmol) of paraformaldehyde and 7.31 g (0.01 mmol) of diethylamine are combined with the same reactants and the same conditions as described above in Example I. This mixture is then refluxed for 48 hours. After the methanol is eliminated as described above in Example I about 24 g of dibutyl dimethyl ethenylidenebisphosphonate is produced as a clear liquid.

EXAMPLE X

This example demonstrates the production of tetra-n-hexyl ethenylidenebisphosphonate.

22.2 g (44.0 mmol) of tetra-n-hexyl methylenebisphosphonate, 6.61 g (220.0 mmol) of paraformaldehyde and 3.22 g (64.0 mmol) of diethylamine are combined with the same reactants and the same conditions as described above in Example I. This mixture is then refluxed for 48 hours. After the methanol is eliminated as described above in Example I, about 17 g of tetra-n-hexyl ethenylidenebisphosphonate is produced as a clear liquid.

EXAMPLE XI

This example demonstrates the production of tetra-n-heptyl ethenylidenebisphosphonate.

56.81 g (44.0 mmol) of tetra-n-heptyl methylenebisphosphonate, 6.61 g (220.0 mmol) of paraformaldehyde and 3.22 g (64.0 mmol) of diethylamine are combined with the same reactants and the same conditions as described above in Example I. This mixture is then refluxed for 48 hours. After the methanol is eliminated as described above in Example I, about 19 g of tetra-n-heptyl ethenylidenebisphosphonate is produced as a clear liquid.

EXAMPLE XII

This example demonstrates the production of methyl tri-n-butyl ethenylidenebisphosphonate,

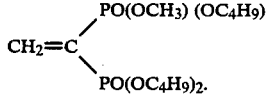

15.77 g (44.0 mmol) of methyl, tri-n-butyl methylenebisphosphonate, 6.61 g (220.0 mmol) of paraformaldehyde and 3.22 g (64.0 mmol) of diethylamine are combined with the same reactants and the same conditions as described above in Example I. This mixture is then refluxed for 48 hours. After the methanol is eliminated as described above in Example I, about 39 g of methyl, tri-n-butyl ethenylidenebisphosphonate is produced as a clear liquid.

EXAMPLE XIII

This example demonstrates the production of ethyl tri-n-hexyl ethenylidenebisphosphonate,

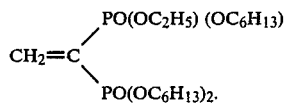

20.09 g (44.0 mmol) of ethyl tri-n-hexyl methylenebisphosphonate, 6.61 g (220.0 mmol) of paraformaldehyde and 3.22 g (64.0 mmol) of diethylamine are combined with the same reactants and the same conditions as described above in Example I. This mixture is then refluxed for 48 hours. After the methanol is eliminated as described above in Example I, about 34 g of ethyl tri-n-hexyl ethenylidenebisphosphonate is produced as a clear liquid.

EXAMPLE XIV

A composition for oral or systemic administration is prepared by combining the following ingredients:

| | |
|---|---|
| tetrabutyl ethenylidenebisphosphonate | 1.5 g |
| Polysorbitan 80 | 7.5 g |
| pyrogen free H$_2$O | 91.0 g |

The tetrabutyl ethenylidenebisphosphonate is dissolved in the polysorbitan 80 and this solution is suspended in the H$_2$O.

From 1.0 ml to 3000 ml of the resulting pharmaceutical composition is administered orally twice daily for three to ten days to a 70 kg human in need of treatment from *Staphylococcus aureus* gastrointestinal infection, curing the infection caused by this bacterium.

From 0.1 ml to 10.0 ml of this same solution can be injected systemically either intravenously, intraperitoneally, intramuscularly, subcutaneously or intradermally to a 70 kg human in need of similar treatment.

These same compositions and dosages will eliminate *Streptococcus mutans* which cause dental caries, *Clostridium Perfringens* which cause gas gangrene, *Escherichia coli* which will cause urinary tract infections and skin infections and other gram-positive and gram-negative pathogenic bacteria.

Substantially similar results are obtained when tetrabutyl ethenylidenebisphosphonate is replaced, in whole or in part, with an equivalent amount of tetramethyl ethenylidenebisphosphonate, tetraethyl ethenylidenebisphosphonate, tetra-n-propyl ethenylidenebisphosphonate, tetraheptyl ethenylidenebisphosphonate, dimethyl diethyl ethenylidenebisphosphonate, dibutyl dimethyl ethenylidenebisphosphonate, methyl tributyl ethenylidenebisphosphonate or ethyl tri-n-hexyl ethenylidenebisphosphonate.

EXAMPLE XV

A composition for topical administration is prepared by combining the following ingredients:

| | |
|---|---|
| tetrabutyl ethenylidenebisphosphonate | 3 g |
| granule dry soap | 10 g |
| H$_2$O | 87 g |

The granule dry soap is added to the water and a soap solution is prepared. The tetraalkyl ethenylidenebisphosphonate is then added under agitation producing a medicated soap solution. Washing twice daily for three to seven days with 240 mg of the resulting soap solution on an 80 cm² portion of the forearm will eliminate infectious agents such as *Staphylococcus aureaus, Escherichia coli* and other gram-positive and gram-negative pathogenic bacteria which are present on the skin.

A substantially similar result is obtained when tetrabutyl ethenylidenebisphosphonate is replaced in whole or in part, with an equivalent amount of tetramethyl ethenylidenebisphosphonate, tetraethyl ethenylidenebisphosphonate, tetra-n-propyl ethenylidenebisphosphonate, tetraheptyl ethenylidenebisphosphonate, dimethyl diethyl ethenylidenebisphosphonate, dibutyl dimethyl ethenylidenebisphosphonate, methyl tributyl ethenylidenebisphosphonate or ethyl tri-n-hexyl ethenylidenebisphosphonate.

EXAMPLE XVI

A capsule for oral administration is prepared by combining the following ingredients:

| | |
|---|---|
| tetrabutyl ethenylidenebisphosphonate | 30 g |
| sesame oil | 70 g |

These ingredients are blended and 150 mg of the resulting solution is placed in a #4 capsule by methods known in the art.

1-2 capsules are administered every 8 hours for three to seven days to a 70 kg human in need of treatment. This dosage will eliminate gram-positive and gram-negative infectious agents as previously described above in Examples XIV and XV.

Substantially similar results are obtained if the tetrabutyl ethenylidenebisphosphonate is replaced, in whole or in part, with an equivalent amount of tetramethyl ethenylidenebisphosphonate, tetraethyl ethenylidenebisphosphonate, tetra-n-propyl ethenylidenebisphosphonate, tetraheptyl ethenylidenebisphosphonate, dimethyl diethyl ethenylidenebisphosphonate, dibutyl dimethyl ethenylidenebisphosphonate, methyl tributyl ethenylidenebisphosphonate or ethyl tri-n-hexyl ethenylidenebisphosphonate.

EXAMPLE XVII

A composition for topical administration is prepared by combining the following ingredients:

| | |
|---|---|
| tetrabutyl ethenylidenebisphosphonate | 5 g |
| polyethylene glycol (mw = 3,000) | 50 g |
| pyrogen-free H₂O | 45 g |

These ingredients are blended to form a cream. Application of 240 mg of the resulting cream to a 80 cm² portion of the forearm of a human in need of treatment twice daily for three to seven days will eliminate gram-positive and gram-negative infectious agents as previously described above in Examples XIV and XV.

Substantially similar results are obtained if the tetrabutyl ethenylidenebisphosphonate is replaced, in whole or in part, with an equivalent amount of tetramethyl ethenylidenebisphosphonate, tetraethyl ethenylidenebisphosphonate, tetra-n-propyl ethenylidenebisphosphonate, tetraheptyl ethenylidenebisphosphonate, dimethyl diethyl ethenylidenebisphosphonate, dibutyl dimethyl ethenylidenebisphosphonate, methyl tributyl ethenylidenebisphosphonate or ethyl tri-n-hexyl ethenylidenebisphosphonate.

EXAMPLE XVIII

A mouthwash composition for oral rinsing is prepared by combining the following ingredients:

| | |
|---|---|
| Tetrabutyl ethenylidenbisphosphonate | 0.5 g |
| Polysorbitan 80 | 1.2 g |
| Mint flavoring | 0.1 g |
| Glycerin | 3.0 g |
| Sodium flouride | 0.5 g |
| Ethanol | 10.0 g |
| Distilled H₂O | 84.7 g |

The tetrabutyl ethenylidenebisphosphonate is dissolved into the polysorbitan 80. The remaining components are then blended into this mixture and a mouthwash solution is prepared.

20 ml of the resulting mouthwash are administered to a human in need of treatment. This dosage will inhibit the growth of *Streptococcus mutans* and other gram-positive pathogenic bacteria thereby preventing dental and root surface carries.

Substantially similar results are obtained if the tetrabutyl ethenylidenebisphosphonate is replaced, in whole or in part, with an equivalent amount of tetramethyl ethenylidenebisphosphonate, tetraethyl ethenylidenebisphosphonate, tetra-n-propyl ethenylidenebisphosphonate, tetraheptyl ethenylidenebisphosphonate, dimethyl diethyl ethenylidenebisphosphonate, dibutyl dimethyl ethenylidenebisphosphonate, methyl tributyl ethenylidenebisphosphonate or ethyl tri-n-hexyl ethenylidenebisphosphonate.

EXAMPLE XIX

A dentifrice composition for topical administration to teeth is prepared by combining the following ingredients:

| | |
|---|---|
| Tetrabutyl ethenylidenebisphosphonate | 0.4 g |
| Glycerin | 67.3 g |
| Silicon dioxide | 20.0 g |
| Xanthan gum | 1.0 g |
| Mint flavor | 1.0 g |
| Titanium dioxide | 0.7 g |
| Sodium fluoride | 0.3 g |
| Distilled H₂O | 6.6 g |

These ingredients are blended to form a cream. Application of 5 g of the resulting dentifrice cream to the teeth of a human in need of treatment will inhibit the growth of *Streptococcus mutans* and other gram-positive pathogenic bacteria thereby preventing dental and root surface carries.

Substantially similar results are obtained if the tetrabutyl ethenylidenebisphosphonate is replaced, in whole or in part, with an equivalent amount of tetramethyl ethenylidenebisphosphonate, tetraethyl ethenylidenebisphosphonate, tetra-n-propyl ethenylidenebisphosphonate, tetraheptyl ethenylidenebisphosphonate, dimethyl diethyl ethenylidenebisphosphonate, dibutyl dimethyl ethenylidenebisphosphonate, methyl tributyl ethenylidenebisphosphonate or ethyl tri-n-hexyl ethenylidenebisphosphonate.

EXAMPLE XX

A shampoo composition for topical administration is prepared by combining the following ingredients:

| | |
|---|---|
| Tetrabutyl ethenylidenebisphosphonate | 4.0 g |
| Sodium dodecylbenzene sulfonate | 1.0 g |
| Sodium toluene sulfonate | 1.0 g |
| Sodium chloride | 1.5 g |
| Distilled H$_2$O | 92.5 g |

The sodium dodecylbenzene sulfonate is added to the distilled water and the resulting mixture is blended until clear. The remaining components are then blended into this solution to form a shampoo composition.

1 g of the resulting shampoo composition is applied to the wetted hair of a human in need of treatment. The shampoo is worked through hair and then rinsed out. This regimen is performed three to five times a week to eliminate gram-positive and gram-negative infectious agents as well as eukaryotic microorganisms such as *Pityrosporon ovale* and *Pityrosporan orbiculare* which cause dandruff.

Substantially similar results are obtained if the tetrabutyl ethenylidenebisphosphonate is replaced, in whole or in part, with an equivalent amount of tetramethyl ethenylidenebisphosphonate, tetraethyl ethenylidenebisphosphonate, tetra-n-propyl ethenylidenebisphosphonate, tetraheptyl ethenylidenebisphosphonate, dimethyl diethyl ethenylidenebisphosphonate, dibutyl dimethyl ethenylidenebisphosphonate, methyl tributyl ethenylidenebisphosphonate or ethyl tri-n-hexyl ethenylidenebisphosphonate.

EXMAPLE XXI

A hard surface cleaning composition is prepared by combining the following ingredients:

| | |
|---|---|
| Tetrabutyl ethenylidenebisphosphonate | 5.0 g |
| Isopropanol | 3.5 g |
| Sodium laureth sulfate | 20.0 g |
| Distilled H$_2$O | 69.5 g |

The tetrabutyl ethenylidenebisphosphonate and the isopropanol are added to the distilled water and blended for 15 minutes to form a solution. The sodium laureth sulfate is then added to this solution and the resulting solution is blended for 10 minutes, producing a hard surface cleanser.

Use of this composition to clean household environmental surfaces such as countertops will eliminate odor-causing agents such as *Staphylococcus aureaus* and other gram-positive and gram-negative bacteria on such surfaces.

Substantially similar results are obtained if the tetrabutyl ethenylidenebisphosphonate is replaced, in whole or in part, with an equivalent amount of tetramethyl ethenylidenebisphosphonate, tetraethyl ethenylidenebisphosphonate, tetra-n-propyl ethenylidenebisphosphonate, tetraheptyl ethenylidenebisphosphonate, dimethyl diethyl ethenylidenebisphosphonate, dibutyl dimethyl ethenylidenebisphosphonate, methyl tributyl ethenylidenebisphosphonate or ethyl tri-n-hexyl ethenylidenebisphosphonate.

Other surfactants such as sodium lauryl sulfate as well as various other optional components such as abrasives (e.g., sodium metasilicate), builders (e.g., potassium pyrophosphate) and suds supressors (e.g., ethoxylated n-decyl alcohol) which are set forth in U.S. Pat. No. 4,414,128 to Goffinet, issued Nov. 8, 1983 and in U.S. Pat. No. 3,679,608 to Aubert et al., issued July 25, 1972, both of which are incorporated herein by reference, can also be used in formulating hard surface cleaner compositions containing the tetraalkyl ethenylidenebisphosphonates of the present invention.

EFFECTIVENESS IN ELIMINATING INFECTION

The in vitro antibacterial activity of several tetraalkyl ethenylidenebisphosphonates, fosfomycin and Penicillin G were tested against various gram-postive and gram-negative bacteria using the standard microdilution Minimum Inhibitory Concentration (MIC) assay as disclosed in *Laboratory Procedures in Clinical Microbiology* (John A. Washington, editor), 281–311 (1985), incorporated herein by reference. The results are presented in the following Table:

| | A | B | C | D | E |
|---|---|---|---|---|---|
| *E. Coli* (G−) Clinical isolate | 520 | 6,300 | 25,000 | 320 | 260 |
| *P. Aeruginosa* (G−) ATCC 27853 Penicillin resistant | 6,300 | 25,000 | 25,000 | 31 | 24,000 |
| *S. Aureus* (G+) ATCC 27660 Penicillin resistant | 1,200 | 160 | 6.5 | 180 | 25,000 |
| *S. Aureus* (G+) ATCC 25923 | 430 | 110 | 4.5 | 56 | 25 |
| *Clostridium* (G+) *perfringens* ATCC 3624 | — | 52 | 2.1 | — | — |
| *S. Aureus* (G+) ATCC 12715 Penicillin resistant | 1,200 | 180 | 6.5 | 72 | 19,000 |
| *Klebsiella* (G−) *Pneumoniae* ATCC | 405 | — | — | — | — |
| *Streptococcus* (G+) *mutans* Clinical isolate | — | — | 1.2 | — | — |
| *Streptococcus* (G+) *mutans* Clinical isolate | — | — | 11 | — | — |
| *Streptococcus* (G+) *mutans* Clinical isolate | — | — | 11 | — | — |

A. Tetrametyl ethenylidenebisphosphonate
B. Tetraethyl ethenylidenebisphosphonate
C. Tetrabutyl ethenylidenebisphosphonate
D. Fosfomycin
E. Penicillin G These in vitro antibacterial activities of the tetraalkyl ethenylidenebisphosphonates demonstrate the broad spectrum efficacy of these compounds against gram-positive and gram-negative microbes. These data also demonstrate that tetrabutyl ethenylidenebisphosphonate is superior to fosfomycin, a clinically well-recognized broad spectrum anti-microbial, in antibacterial efficacy against gram-positive microorganisms. Furthermore, this Table demonstrates that these compounds are efficacious against gram-positive microorganisms which are resistant to Penicillin G.

What is claimed is:

1. A method for synthesizing tetraalkyl ethenylidenebisphosphonates comprising the steps of:
   (a) combining from about 20 to about 96 mole percent of a formaldehyde or formaldehyde precursor selected from the group consisting of formaldehyde, paraformaldehyde or trioxane; from about 2 to about 40 mole percent of a secondary amine; and from 2 to about 40 mole percent of a tetraalkyl methylenebisphosphonate of the formula:

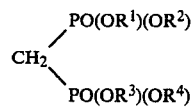

wherein $R^1$, $R^2$, $R^3$ and $R^4$ are independently chosen from the group consisting of $C_1$ to $C_7$ straight or branched alkyl; in an alcohol solvent selected from the group consisting of methanol and ethanol;
(b) heating said mixture to a temperature of from about 40° C. to about 80° C., for a period of from about 0.5 hours to about 200 hours;
(c) replacing said alcohol solvent with an equivalent amount a of solvent selected from the group consisting of toluene, benzene and xylene; and
(d) adding a catalytic amount of an acid selected from the group consisting of paratoluenesulfonic acid and phosphoric acid, and allowing said mixture to react for a period of from about 2 hours to about 48 hours.

2. A method according to claim 1 wherein the secondary amine in step (a) is selected from the group consisting of pyrrolidone, piperidine, diethylamine, dimethylamine, benzylmethylamine, dibenzylamine, di-n-butylamine, dicyclohexylamine, di-n-hexylamine, diisobutylamine, diisopropylamine, di-n-octylamine, piperazine or mixtures thereof, and wherein the alcohol solvent is methanol.

3. A method according to claim 2 wherein the formaldehyde precursor is paraformaldehyde and wherein the amount of said paraformaldehyde is from about 50 to about 80 mole percent, the amount of the amine is from about 10 to about 20 mole percent and the amount of the tetraalkyl methylene bisphosphonate is from about 10 to about 20 mole percent.

4. A method according to claim 3, wherein the amount of paraformaldehyde is from about 50 to about 75 mole percent, the amount of the secondary amine is from about 10 to about 15 mole percent and the amount of tetraalkyl methylene bisphosphonate is from about 10 to about 15 mole percent.

5. A method according to claim 4 wherein the tetraalkyl methylenebisphosphonate is selected from the group consisting of
tetramethyl methylenebisphosphonate,
tetraethyl methylenebisphosphonate,
tetraisopropyl methylenebisphosphonate,
tetra-n-propyl methylenebisphosphonate,
tetra-n-butyl methylenebisphosphonate,
tetra-n-pentyl methylenebisphosphonate,
tetra-n-hexyl methylenebisphosphonate,
tetra-n-heptyl methylenebisphosphonate,
diethyl dibutyl methylenebisphosphonate,
dimethyl di-n-propyl methylenebisphosphonate,
dimethyl diisopropyl methylenebisphosphonate,
dimethyl di-n-butyl methylenebisphosphonate,
diethyl di-n-propyl methylenebisphosphonate,
diethyl diisopropyl methylenebisphosphonate,
diethyl dimethyl methylenebisphosphonate,
diethyl diisobutyl methylenebisphosphonate,
dimethyl di-n-pentyl methylenebisphosphonate,
diethyl di-n-pentyl methylenebisphosphonate
dimethyl di-n-hexyl methylenebisphosphonate,
dimethyl di-n-heptyl methylenebisphosphonate,
diethyl di-n-hexyl methylenebisphosphonate,
diethyl di-n-heptyl methylenebisphosphonate,
di-n-propyl di-n-butyl methylenebisphosphonate,
di-n-propyl di-n-pentyl methylenebisphosphonate,
methyl triethyl methylenebisphosphonate,
methyl tri-n-propyl methylenebisphosphonate,
methyl triisopropyl methylenebisphosphonate,
methyl tri-n-butyl methylenebisphosphonate,
methyl tri-n-pentyl methylenebisphosphonate,
methyl tri-n-hexyl methylenebisphosphonate,
methyl tri-n-heptyl methylenebisphosphonate,
ethyl tri-methyl methylenebisphosphonate,
ethyl tri-n-propyl methylenebisphosphonate,
ethyl tri-n-butyl methylenebisphosphonate,
ethyl tri-n-pentyl methylenebisphosphonate,
ethyl tri-n-hexyl methylenebisphosphonate and
ethyl tri-n-heptyl methylenebisphosphonate,
or mixtures thereof.

6. A method according to claim 5 wherein the amine is selected from the group consisting of diethylamine, piperdine and pyrrolidine.

7. A method according to claim 6 wherein the amine is diethylamine.

8. A method according to claim 6 wherein the reactants in step (b) are heated to a temperature of from about 55° C. to about 75° C.

9. A method according to claim 8 wherein the acid catalyst is paratoluenesulfonic acid.

* * * * *